US00PP21694P2

(12) United States Plant Patent
Oudshoorn

(10) Patent No.: US PP21,694 P2
(45) Date of Patent: Feb. 1, 2011

(54) *PHYGELIUS* PLANT NAMED 'LEMON TEARDROPS'

(50) Latin Name: *Phygelius rectus*
Varietal Denomination: Lemon Teardrops

(75) Inventor: Hubertus Gerardus Oudshoorn, Rijpwetering (NL)

(73) Assignee: Future Plants Licentie B.V., Lisserbroek (NL)

( * ) Notice: Subject to any disclaimer, the term of this patent is extended or adjusted under 35 U.S.C. 154(b) by 0 days.

(21) Appl. No.: 12/587,123

(22) Filed: Oct. 1, 2009

(51) Int. Cl.
*A01H 5/00* (2006.01)

(52) U.S. Cl. ..... Plt./468

(58) Field of Classification Search ..... Plt./263, Plt./468

See application file for complete search history.

*Primary Examiner*—Susan B McCormick Ewoldt
(74) *Attorney, Agent, or Firm*—C. A. Whealy

(57) ABSTRACT

A new and distinct cultivar of *Phygelius* plant named 'Lemon Teardrops', characterized by its upright and outwardly spreading plant habit; moderately vigorous growth habit; numerous light yellow-colored flowers; and good garden performance.

2 Drawing Sheets

Botanical designation: *Phygelius rectus.*
Cultivar denomination: 'LEMON TEARDROPS'.

BACKGROUND OF THE INVENTION

The present invention relates to a new and distinct cultivar of *Phygelius* plant, botanically known as *Phygelius rectus* and hereinafter referred to by the name 'Lemon Teardrops'.

The new *Phygelius* plant is a product of a planned breeding program conducted by the Inventor in Rijpwetering, The Netherlands. The objective of the breeding program is to create new *Phygelius* cultivars with numerous attractive flowers.

The new *Phygelius* plant originated from a cross-pollination in August, 2006 in Rijpwetering, The Netherlands, of two unnamed selections of *Phygelius rectus*, not patented. The new *Phygelius* was discovered and selected by the Inventor as a single flowering plant within the progeny of the stated cross-pollination in a controlled environment in Rijpwetering, The Netherlands in July, 2007.

Asexual reproduction of the new *Phygelius* plant by softwood cuttings in a controlled environment in Rijpwetering, The Netherlands since July, 2007, has shown that the unique features of this new *Phygelius* plant are stable and reproduced true to type in successive generations.

SUMMARY OF THE INVENTION

Plants of the new *Phygelius* have not been observed under all possible environmental conditions. The phenotype may vary somewhat with variations in environment such as temperature and light intensity without, however, any variance in genotype.

The following traits have been repeatedly observed and are determined to be the unique characteristics of 'Lemon Teardrops'. These characteristics in combination distinguish 'Lemon Teardrops' as a new and distinct cultivar of *Phygelius:*

1. Upright and outwardly spreading plant habit.
2. Moderately vigorous growth habit.

3. Numerous light yellow-colored flowers.
4. Good garden performance.

Plants of the new *Phygelius* differ primarily from plants of the parent selections in flowering habit as plants of the new *Phygelius* are more freely flowering than plants of the parent selections.

Plants of the new *Phygelius* can be compared to plants of *Phygelius aequalis* 'Yellow Trumpet', not patented. Plants of the new *Phygelius* and 'Yellow Trumpet' differ in the following characteristics:

1. Plants of the new *Phygelius* have lighter yellow-colored flowers than plants of 'Yellow Trumpet'.
2. Plants of the new *Phygelius* are more hardy than plants of 'Yellow Trumpet'.

BRIEF DESCRIPTION OF THE PHOTOGRAPHS

The accompanying colored photographs illustrate the overall appearance of the new *Phygelius* plant, showing the colors as true as it is reasonably possible to obtain in colored reproductions of this type. Colors in the photographs may differ slightly from the color values cited in the detailed botanical description which accurately describe the colors of the new *Phygelius* plant.

The photograph on the first sheet comprises a side perspective view of typical flowering plants of 'Lemon Teardrops' grown in an outdoor nursery container.

The photograph at the top of the second sheet is a close-up view of a typical flower of 'Lemon Teardrops'.

The photograph at the bottom of the second sheet is a close-up view of the upper surface of a typical leaf of 'Lemon Teardrops'.

DETAILED BOTANICAL DESCRIPTION

The aforementioned photographs and following observations, measurements and values describe plants grown in Rijpwetering, The Netherlands, under commercial practice during the late summer in an outdoor nursery with day temperatures ranging from 14° C. to 32° C. and night temperatures ranging from 6° C. to 18° C. Plants used in the photographs and description were two years old. In the following description, color references are made to The Royal Horticultural Society Colour Chart, 2007 Edition, except where general terms of ordinary dictionary significance are used.

Botanical classification: *Phygelius rectus* 'Lemon Teardrops'.

Parentage:

*Female, or seed, parent.*—Unnamed selection of *Phygelius rectus*, not patented.

*Male, or pollen, parent.*—Unnamed selection of *Phygelius rectus*, not patented.

Propagation:

*Type.*—By softwood cuttings.

*Time to initiate roots.*—About four weeks at 14° C. to 32° C.

*Time to produce a rooted young plant.*—About 200 days months at 10° C. to 28° C.

*Root description.*—Medium in thickness and moderately fleshy; light greyed brown in color.

*Rooting habit.*—Moderately freely branching; medium density.

Plant description:

*Plant form/habit.*—Herbaceous perennial; upright and outwardly spreading plant habit; broad inverted triangle; moderately vigorous growth habit; freely basally branching habit with about five basal branches developing per plant.

*Plant height.*—About 67 cm.

*Plant width (spread).*—About 55.5 cm.

*Lateral branches.*—Length: About 29.9 cm. Diameter: About 5 mm. Internode length: About 3.4 cm. Strength: Strong. Texture: Smooth, glabrous. Color: Close to 146C.

Foliage description:

*Arrangement.*—Opposite, simple.

*Length.*—About 8.8 cm.

*Width.*—About 4.7 cm.

*Shape.*—Ovate.

*Apex.*—Bluntly acute.

*Base.*—Obtuse.

*Margin.*—Serrate.

*Texture, upper and lower surfaces.*—Smooth, glabrous.

*Venation pattern.*—Pinnate.

*Color.*—Developing leaves, upper surface: Close to 137A. Developing leaves, lower surface: Close to 138B to 138C. Fully expanded leaves, upper surface: Between 137A and 139A; venation, close to 144A. Fully expanded leaves, lower surface: Close to N138C; venation, close to 144B.

*Petioles.*—Length: Close to 3.5 cm. Diameter: Close to 2 mm. Texture, upper and lower surfaces: Smooth, glabrous. Color, upper surface: Close to 146B. Color, lower surface: Close to 144A.

Flower description:

*Flower type and habit.*—Single salverform flowers arranged in terminal panicles; freely flowering habit, usually about 60 flowers per panicle; flowers elongated and pendulous.

*Fragrance.*—Not detected.

*Natural flowering season.*—Flowering continuous from mid-July to late September in The Netherlands; plants commence flowering about nine months after planting.

*Flower longevity.*—Flowers last about one week on the plant; flowers not persistent.

*Inflorescence height.*—About 37.2 cm.

*Inflorescence width.*—About 12.6 cm.

*Flower diameter.*—About 1.8 cm.

*Flower length.*—About 6.4 cm.

*Flower buds.*—Length: About 3.8 cm. Diameter: About 8 mm. Shape: Narrowly oblong to obovate. Color: Close to 1C to 1D.

*Corolla.*—Shape/arrangement: Tubular; five fused petals; petals are free on distal 17.5% of tube. Petal apex: Broadly acute. Petal margin: Entire; revolute. Petal length: About 4.5 cm. Petal width: About 7 mm. Petal texture, upper and lower surfaces of petal lobes: Smooth, glabrous. Petal color: When opening, inner surface: Tube, close to 2D; towards the apex, close to 1C. When opening, outer surface: Tube, close to 2C tinged with close to 39D; towards the apex, close to 2B to 2C. Fully opened, inner surface: Tube, close to 2D; towards the apex, close to 1C. Fully opened, outer surface: Tube, close to 2D; towards the apex, close to 1C.

*Calyx.*—Shape/arrangement: Campanulate; five fused sepals; sepals are free on distal 20% of tube. Length: About 7 mm. Diameter: About 1 cm. Sepal apex: Acute. Sepal margin: Entire. Sepal length: About 7 mm. Sepal width: About 3 mm. Sepal texture, upper and lower surfaces: Smooth, glabrous. Sepal color, inner surface: Close to 143B to 143C. Sepal color, outer surface: Close to 137A.

*Peduncles.*—Length: About 36.9 cm. Diameter: About 3 mm. Strength: Strong. Angle: Primary flowering stems, erect; secondary flowering stems, about 55° from the stem. Color: Close to 146A, may be tinged with close to N199A.

*Pedicels.*—Length: About 1.6 cm. Diameter: About 1 mm. Strength: Strong. Angle: About 30° from the stem. Color, upper surface: Close to 183A. Color, lower surface: Close to 144A to 144B.

*Reproductive organs.*—Androecium: Stamen quantity: Four per flower; basifixed. Filament length: About 1.7 cm. Filament color: Close to 2D. Anther length: About 3 mm. Anther shape: Oval. Anther color: Close to 197A. Pollen amount: Scarce. Pollen color: Darker than 195A. Gynoecium: Pistil quantity: One per flower. Pistil length: About 5.8 cm. Style length: About 5.7 cm. Style color: Close to 148D. Stigma shape: Club-shaped. Stigma color: Close to 143A. Ovary color: Close to 143C.

*Seed/fruit.*—Seed and fruit development have not been observed.

Disease/pest resistance: Plants of the new *Phygelius* have not been noted to be resistant to pathogens and pests common to *Phygelius*.

Garden performance: Plants of the new *Phygelius* have been observed to have good garden performance and tolerate rain and wind. Plants of the new *Phygelius* tolerate high temperatures of about 35° C. and are winter hardy to USDA Hardiness Zone 7.

It is claimed:

1. A new and distinct *Phygelius* plant named 'Lemon Teardrops' as illustrated and described.

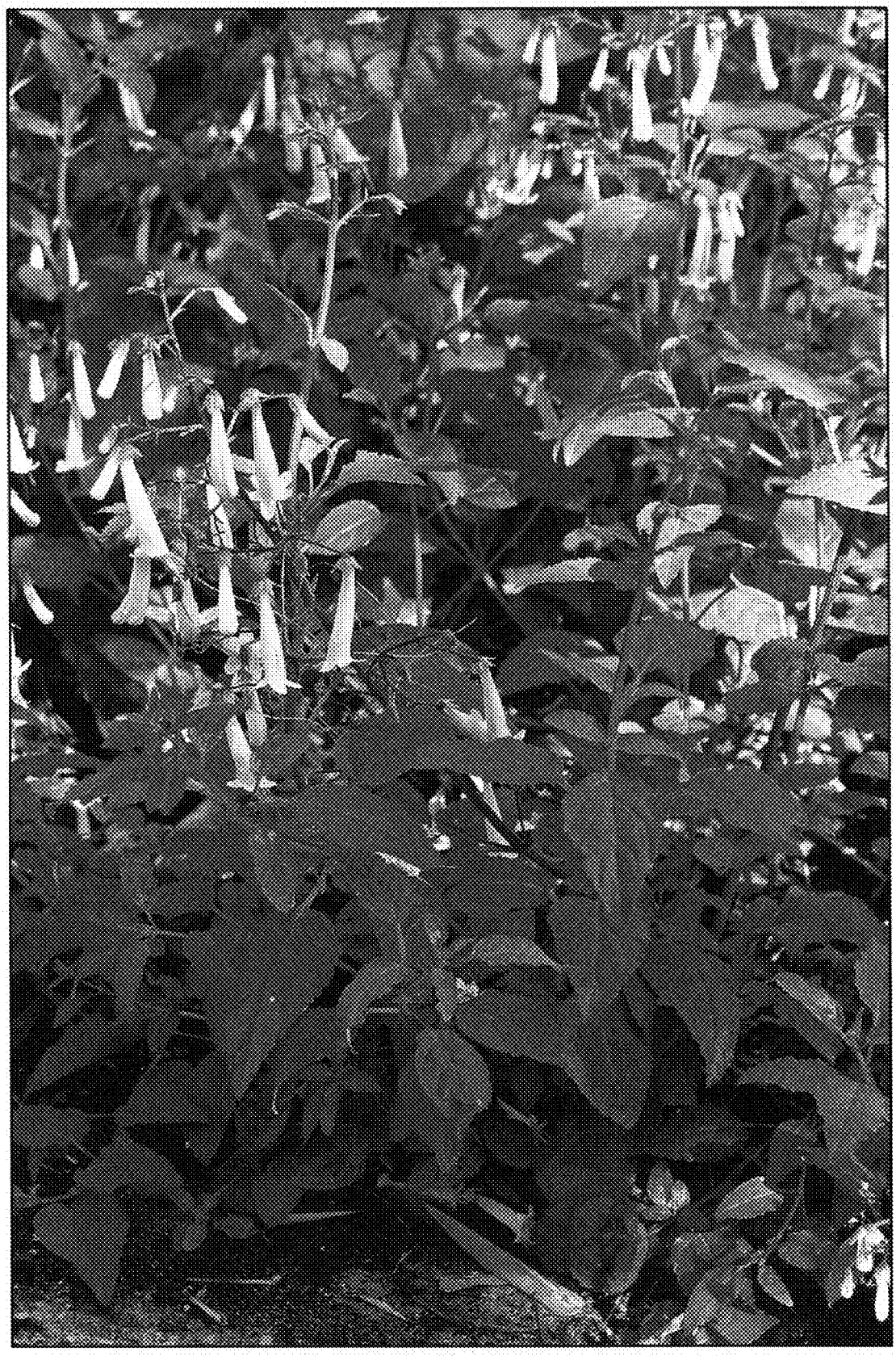

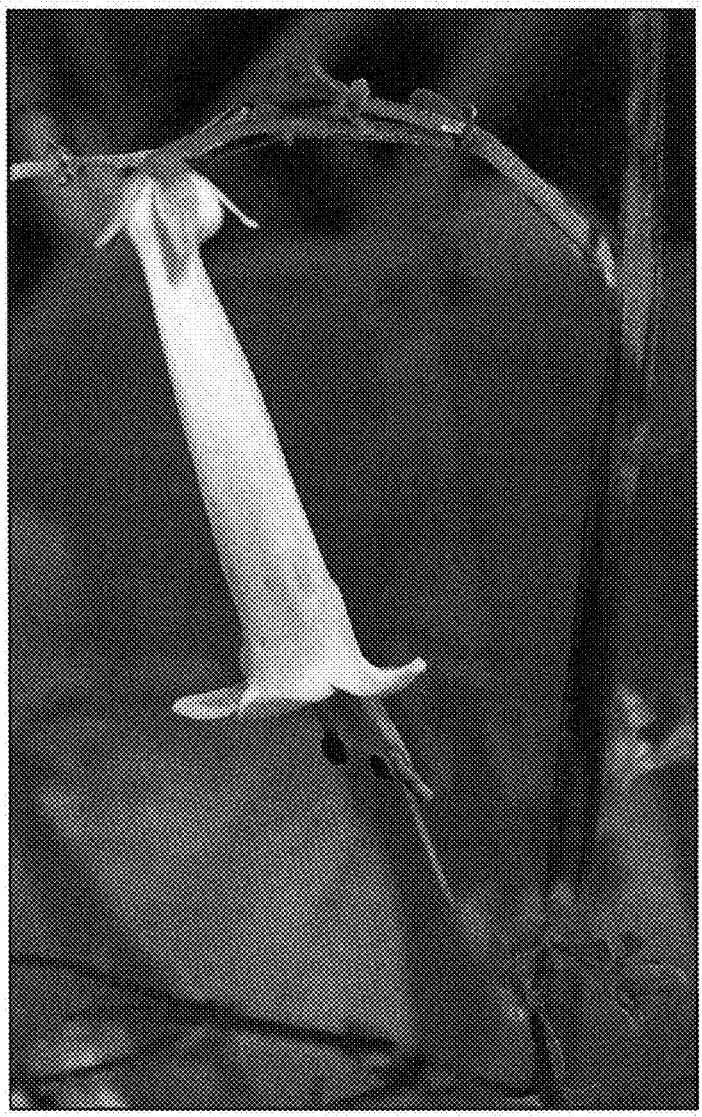
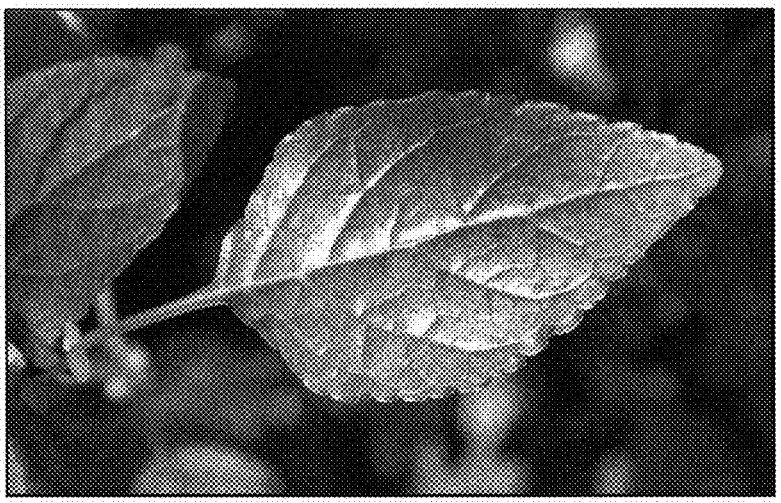

* * * * *